(12) United States Patent
Chao

(10) Patent No.: US 6,173,034 B1
(45) Date of Patent: Jan. 9, 2001

(54) METHOD FOR IMPROVED BREAST X-RAY IMAGING

(75) Inventor: Yong-Sheng Chao, Storrs, CT (US)

(73) Assignee: Advanced Optical Technologies, Inc., E. Hartford, CT (US)

( * ) Notice: Under 35 U.S.C. 154(b), the term of this patent shall be extended for 0 days.

(21) Appl. No.: 09/235,912

(22) Filed: Jan. 25, 1999

(51) Int. Cl.[7] .................................................... A61B 6/04
(52) U.S. Cl. ................................. 378/37; 378/62; 378/98.9
(58) Field of Search ................................. 378/37, 53, 62, 378/98.8, 98.9

(56) References Cited

U.S. PATENT DOCUMENTS

| | | | | |
|---|---|---|---|---|
| 4,349,739 | * | 9/1982 | Annis ................................. | 378/98.5 |
| 5,365,429 | * | 11/1994 | Carman ................................ | 378/37 |

OTHER PUBLICATIONS

Hamid Jafroudi, *Dual–Energy in Mammography—Feasibility Study*, 2708 Proc. of the SPIE 278 (Feb. 1996).

Paul C. Johns et al., *Dual–Energy Mammography: Initial Experimental Results*, 12 Medical Physics 297 (May/Jun. 1985).

Dev P. Chakraborty et al., *An Energy Sensitive Cassette for Dual–Energy Mammography*, 16 Medical Physics 7 (Jan./Feb. 1989).

Stephen A. Feig et al., *Digital Mammography, Computer–Aided Diagnosis, and Telemammography*, vol. 33, No. 6 Radiologic Clinics of North America 1205 (Nov. 1995).

Paul C. Johns et al., *Theoretical Optimization of Dual–Energy X–Ray Imaging with Application to Mammography*, 12 Medical Physics 289 (May/Jun. 1985).

Carey E. Floyd, Jr. et al., *Quantitative Scatter Measurement in Digital Radiography Using a Photostimulable Phosphor Imaging System*, 18 Medical Physics 408 (May/Jun. 1991).

* cited by examiner

Primary Examiner—David V. Bruce
(74) Attorney, Agent, or Firm—Morse, Altman & Martin (57) ABSTRACT

A method for performing dual-energy x-ray imaging of a human breast including separating the breast image into five basic first order approximation image components: a dual-energy scatter image pair, a lean tissue image, a fat tissue image, and a microcalcification image. In the second order approximation, lean tissue image and fat tissue image are adjusted to correct for the microcalcification component so that each contains only a single breast component. The method also includes a calibration method so that the materials used are the actual breast tissues, instead of merely equivalent materials.

7 Claims, 4 Drawing Sheets

METHOD FOR IMPROVED BREAST X-RAY IMAGING

BACKGROUND OF THE INVENTION

1. Field of the Invention

The present invention relates generally to digital xray imaging and, more particularly, to a method of digital mammography that uses dual-energy apparatus and methods for separating a single human breast x-ray image into component images, each representing a single physical substance.

2. The Prior Art

Typical clinical mammography is performed by using x-ray films. Recently, large format two-dimensional semiconductor digital x-ray detector arrays have been available. Currently, regardless of the technology, all of the image information is contained in a single image, acquired through the use of x-rays with a single energy-spectrum. The human breast is comprised of three major substances, the lean tissue, the fat tissue, and microcalcification deposits, and each pixel of such a single image contains a mixture of all three, plus a random scatter component. The size of the contribution from each component is not known in current mammography.

It is well established that the role of the random scatter signal in an x-ray imaging is interference and distortion. The scatter blurs the image, reduces the image contrast, and degrades the image quality. The contribution of scatter in mammography is generally as high as 30% to 60% of the total image signal.

It has also been established by breast cancer research, that the cancer cells have an x-ray attenuation coefficient very close to that of glandular duct which has an average composition of typical lean tissue. Thus, only the lean tissue component provides useful information for the diagnosis of cancer. The direct value of the fat tissue information for the diagnosis is very small. At the same time, the fat tissue or adipose tissue occupies as much as about 50% of the total breast volume and is closely mingled with the lean tissue. Thus, in mammography, the fat tissue signal also acts more as an adverse factor, imposing a strong, irregular pattern to mask the useful information.

The image signal of lean tissue is used for direct determination of breast cancer or other pathological changes. The microcalcification component is an important reference because it has been found that most breast cancer patients have a large amount of microcalcification in breast tissue.

Because of the inability to separate the four basic signal components, the capability of current x-ray imaging for cancer diagnosis has been essentially limited.

The present invention is based on the dual-energy x-ray imaging method disclosed in U.S. Pat. Nos. 5,648,997 and 5,771,269 and U.S. patent application Ser. No. 09/025,926 (the Chao disclosures). In terms of the prior art, the applicability of dual-energy x-ray imaging to mammography is discussed in several journal articles. The method and apparatuses used in these articles are essentially different from the present invention. For example, Chakraborty et al. (An Energy Sensitive Cassette for Dual-Energy Mammography, 16(1) Medical Physics 7 (January/February 1989)) designed a double film cassette to use a "dual-energy subtraction method" for enhancing image contrast. Johns and Yaffe (Theoretical Optimization of Dual-Energy x-Ray Imaging with Application to Mammography, 12(3) Medical Physics 289 (May, June 1985)) conducted experiments using linear detector arrays and linearization approximations for dual energy decomposition. First, the hardware between these references and the Chao disclosures is different; the detectors of the prior art are either film cassettes, linear detector arrays, or stimulable phosphor plates. Using an intermediate digitizing method to convert the analog image data either from x-ray films or from stimulable phosphor plates into a digital format is essentially a semi-quantitative imaging system. The present invention uses two-dimensional large format integrated semiconductor detectors for direct high-accuracy quantitative imaging. Secondly, the dual-energy decomposition in the prior art is invariably based on linearization methods, while the present invention is based on directly solving a dual-energy fundamental equation system in its original form without relying on linearization. Thirdly, the present invention uses imaging hardware which combines scatter removal capability and dual-energy data acquisition in one system.

SUMMARY OF THE INVENTION

An object of the present invention is to provide a method for enhancing the diagnosis value of x-ray images for mammography.

The present invention provides a method for quantitatively separating a breast x-ray image into a number of component images: the scatter image, the fat tissue image, the lean tissue image, and the microcalcification image. The present invention uses dual-energy x-ray imaging system hardware configurations as described in U.S. Pat. Nos. 5,648,997 and 5,771,269 and U.S. patent application Ser. No. 09/025,926 (the Chao disclosures), incorporated herein by reference. The present invention does not provide any new hardware.

As to the method of the present invention, the basic methods for removing scatter and for dual-energy decomposition described in the Chao disclosures are used, and are not an aspect of the present invention. However, the method of the present invention includes significant improvements and is not a simple implementation of these patented methods. To separate the three material composition by using the basic dual-energy method, new procedures are required. The present invention provides a systematic method to achieve decomposition of a breast image into multiple component images according to physical substance.

The method of the present invention is to use the basic method for removal of scatter and the basic method for dual-energy x-ray imaging to first separate a mixed breast image into four basic image components: a scatter image, a lean tissue image, a fat tissue image, and a microcalcification image. "Microcalcification" is used interchangeably with "calcification". These images are a first order approximation. Then the three material compositions of the human breast are taken into account. In the second order approximation, the microcalcification image, lean tissue image, and fat tissue image are separated so that each contains only a single breast component.

The method of obtaining the first order approximations includes the steps of (a) performing a calibration, as described below, to obtain a pair of numerical relationships for the front detector at the high and low energies for the microcalcification c and the soft tissue s to obtain the functions $c=c(D_H,D_L)$ and $s=s(D_H,D_L)$, (b) perform a calibration to obtain a pair of numerical relationships for the front detector at the high and low energies for the fat tissue f and the lean tissue g to obtain the functions $f=f(D_H,D_L)$ and $g=g(D_H,D_L)$, (c) illuminating the subject with x-rays of said average energy level H and of average energy L, (d) acquiring high-resolution images $D_{fHh}(x,y)$ and $D_{fLh}(x,y)$ from the front detection locations (x,y), where the images are composed of both primary and scatter x-rays, (e) calculating a pair of high-resolution scatter x-ray images $D_{fSHh}(x,y)$ and $D_{fSLh}(x,y)$, (f) calculating a pair of high-resolution primary x-ray images $D_{fPHh}(x,y) = D_{fHh}(x,y) - D_{fSHh}(x,y)$ and $D_{fPLh}(x,y) = D_{fLh}(x,y) - D_{fSLh}(x,y)$ (g) performing a dual-energy decomposition for the image pair $D_{fPHh}(x,y)$ and $D_{fPLh}(x,y)$ using the functions $c=c(D_H,D_L)$ and $s=s(D_H,D_L)$ to obtain two first order approximation material composition images $c_1(x,y)$ and $s_1(x,y)$, and (h) performing a dual-energy decomposition for the image pair $D_{fPHh}(x,y)$ and $D_{fPLh}(x,y)$ using the functions $f=f(D_H,D_L)$ and $g=g(D_H,D_L)$ to obtain two first order approximation material composition images $f_1(x,y)$ and $g_1(x,y)$.

The method of obtaining the second order approximations corrects for microcalcification effects and includes the steps of (a) identifying all microcalcification points $c_1(x_k,y_k)$ and all non-microcalcification points $c_1(x_i,y_i)$ in the image $c_1(x,y)$, (b) constructing a background image $B(x,y)$ where points $B(x_i,y_i)=c_1(x_i,y_i)$ and where points $B(x_k,y_k)$ are interpolated from points $c_1(x_j,y_j)$ around points $C_1(x_k,y_k)$, (c) subtracting the background image $B(x,y)$ from the image $c_1(x,y)$ to obtain a second order approximation microcalcification image $c_2(x,y)$, (d) identifying all zero points $c_2(x_o,y_o)$ and non-zero points $c_2(x_m,y_m)$ in the image $c_2(x,y)$; (e) constructing a second order approximation fat tissue image $f_2(x,y)$ where points $f_2(x_o,y_o)=f_1(x_o,y_o)$ and where points $f_2(x_m,y_m)$ are interpolated from points $f_1(x_n,y_n)$ around points $f_1(x_m,y_m)$; and (f) constructing a second order approximation lean tissue image $g_2(x,y)$ where points $g_2(x_o,y_o)=g_1(x_o,y_o)$ and where points $g_2(x_m,y_m)$ are interpolated from points $g_1(x_n,y_n)$ around points $g_1(x_m, y_m)$.

Another object of the present invention is to provide an improved dual-energy calibration method so that the decomposed two materials are the actual breast tissue components, instead of merely equivalent materials. Currently, dual-energy calibration is performed by measuring x-ray attenuation curves using attenuation plates of a pair of different materials having known values of thickness. Generally, the materials used for calibration cannot be the same as those actually present in the human body, because the actual substances in the human body are too complex to be made as quantitative materials. For example, it is a common practice to use aluminum as a representation of human bone material and to use Lucite as a representation of human average soft tissue. Thus, the dual-energy results can only provide an equivalent aluminum quantity and an equivalent Lucite quantity in terms of x-ray attenuation in the human body. By using the standard calibration method and the equivalent decomposition, the second order approximation of the present invention cannot be achieved. Thus, the improved dual-energy calibration method is part of the present invention for a high accuracy decomposition of the human breast into pure single-component images.

The calibration method of the present invention includes the steps of (1) determining a dual-energy equation system for two known materials u and v as $D_H=D_{DH}[u,v]$, $D_L=D_{DL}[u,v]$, (2) conducting functional decomposition for energy-dependent attenuation coefficient functions $\mu_u(E)=u_p \times \mu_p(E)+u_q \times \mu_q(E)$ and $\mu_v(E)=v_p \times \mu_p(E)+v_q \times \mu_q(E)$ using standard least-square data fitting methods to obtain constants $u_p$, $u_q$, $v_p$, and $v_q$, (3) calculating $u \times (u_p+v_p)=p$ and $v \times (u_q+v_q)=q$ for each coordinate pair (u,v) to obtain dual-energy equation system $D_H=D_{DH}[p,q]$, $D_L=D_{DL}[p,q]$, and (4) solving the equation system $D_H=D_{DH}[p,q]$, $D_L=D_{DL}[p,q]$ for the materials p and q as a function of variable pair $(D_H,D_L)$ through numerical inversion to obtain the equation system $p=p[D_H, D_L]$ and $q=q[D_H,D_L]$. This calibration is performed for the component pair microcalcification and the soft tissue, which is an average combination of fat tissue and lean tissue, and is then performed for the component pair fat tissue and lean tissue.

Other objects of the present invention will become apparent in light of the following drawings and detailed description of the invention.

BRIEF DESCRIPTION OF THE DRAWINGS

For a fuller understanding of the nature and object of the present invention, reference is made to the accompanying drawings, wherein.

DETAILED DESCRIPTION

Hardware

Figure 1:
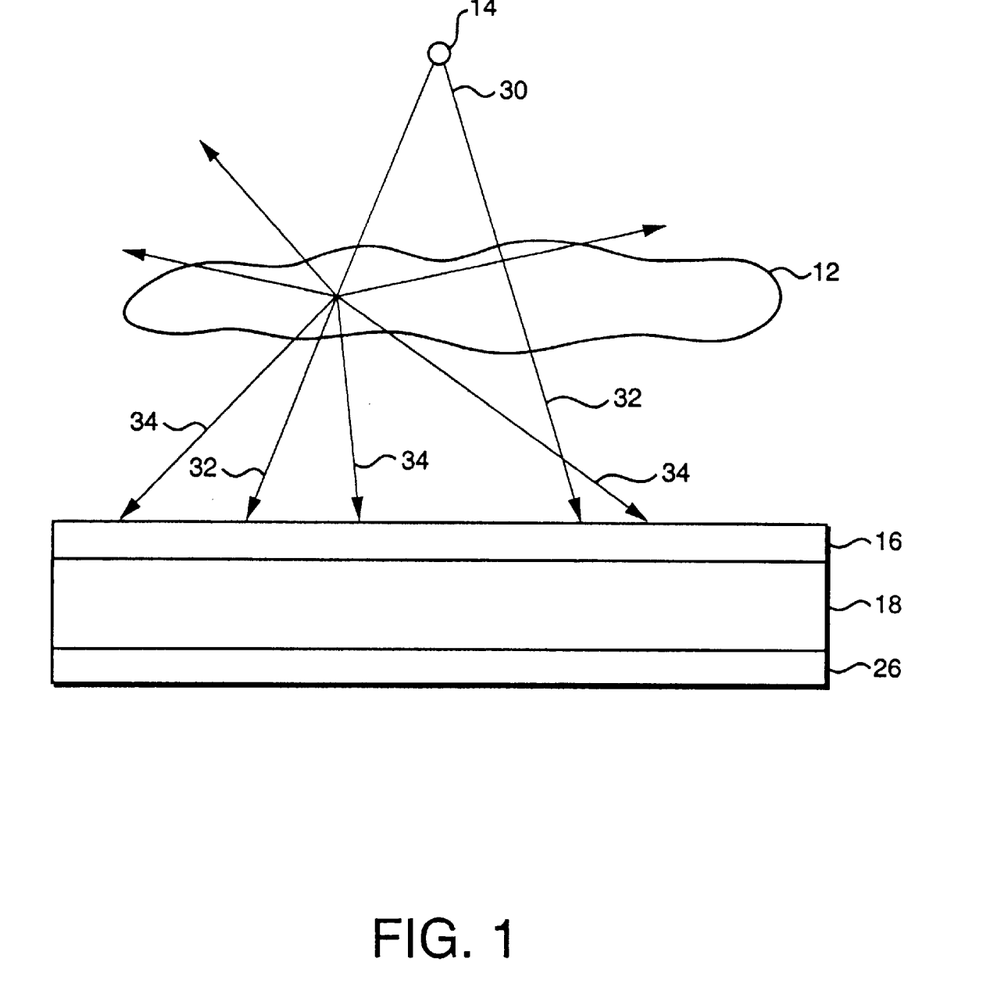
FIG. 1 is a schematic presentation of the hardware system of the present invention.

The dual-energy breast x-ray imaging system of the present invention has two hardware configurations as described in the Chao disclosures, one described in U.S. Pat. Nos. 5,648,997 and 5,771,269 and the other described in U.S. patent application Ser. No. 09/025,926, all of which are incorporated herein by reference. The present invention utilizes these hardware configurations without change. The common features of the two configurations, as shown in FIG. 1, include a dual energy x-ray source 14, a front detector 16, a beam selector 18, and a rear detector 26. The subject under examination 12 is located between the x-ray source 14 and the front detector 16. The x-ray source 14 emits two consecutive pulses, a high-energy pulse at an average energy level H followed by a low-energy pulse at an average energy level L. Each pulse has a single energy spectrum, which is composed of bremsstrahlung radiation and discrete line emissions. A single energy x-ray spectrum generally cannot be represented by a single energy value, but has an distributed energy range. With the emission of each x-ray pulse, the front detector records a composite high-spatial-resolution image, the rear detector records one or two low-spatial-resolution images, depending upon the specific beam selector used.

A portion of the x-rays 32 passes through the subject 12 directly to the front detector assembly 16 without a change in their direction of propagation. These x-rays 32 are called the primary x-rays and convey true information about the subject 12. The remainder of the x-rays 34 are randomly scattered as a result of interaction with the material of the subject 12. These x-rays 34 are called scatter and cause a distortion of the true information.

There are two types of beam selectors: type I and type II beam selectors. The type I beam selector blocks all scatter, allowing only primary x-rays to be detected by the rear detector array at a number of selected locations (i,j). From a pair of dual-energy images recorded by the rear detector at the selected locations (i,j), the scatter images at the two energy levels for the front detector can be calculated. Then, a pair of high-spatial-resolution primary images at the front detector can be calculated. By using the dual-energy data decomposition method as described in U.S. Pat. Nos. 5,648, 997 and 5,771,269, two material composition images can be calculated.

The type II beam selector blocks primary x-rays from a number of locations on the rear detector and allows both primary x-rays and scatter to other locations of the rear detector. From these two images, the dual-energy primary x-ray images at selected locations (i,j) on the rear detector can be calculated. Once these images are determined, the process is the same as that for the type I beam selector configuration.

Method

The method of the present invention comprises a number of parts. The first is a preliminary decomposition of a mixed-component breast x-ray image into five component images: the high-energy scatter image data, the low-energy scatter image data, the fat tissue image, the lean tissue image, and the microcalcification image. This part uses the scatter removal method and the dual-energy decomposition method as described in the Chao disclosures. However, the calibration method is new, and is an aspect of the present invention. The new calibration method allows the dual-energy decomposition to provide true breast tissue component images, instead of aluminum equivalent or Lucite equivalent material images. As a result, the five component images are a reasonably good representation of human breast information. However, important further improvements can still be made, because the human breast is composed of three tissue components, a simple dual-energy decomposition still has some limitations. Some of the component images obtained in the first part of the procedure still contain a small portion of mixed signals, and are not a pure single-component image. These preliminary image data in five image components is denoted as a first order approximation.

The second part of the method of the present invention provides more accurate single-component images for use in medical diagnosis. The result is the second order approximation.

First Order Approximation

Figure 2:
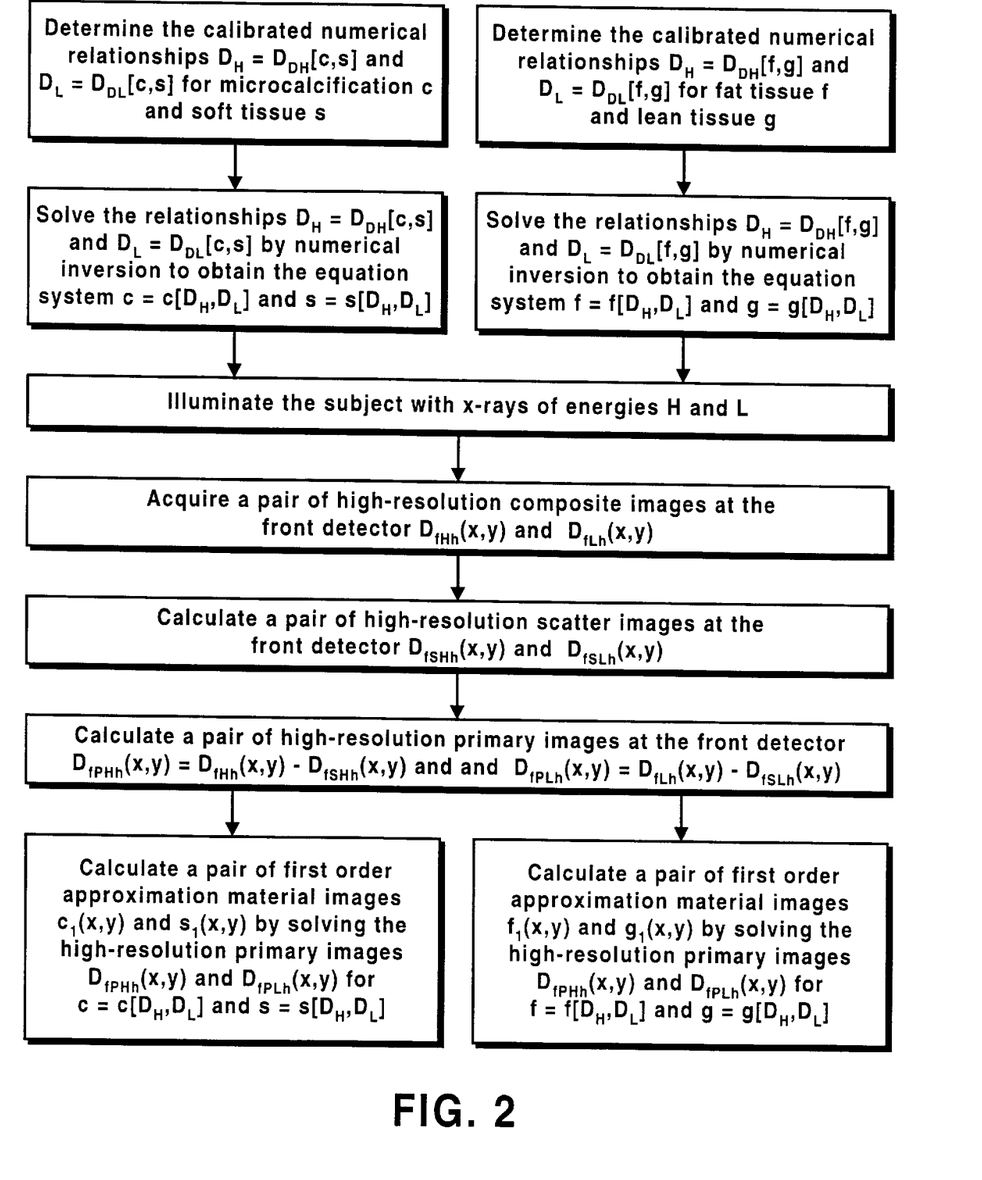
FIG. 2 is a flow diagram of the method for performing a decomposition of a breast image into first order component images.

The steps of the first order approximation are shown in the flow diagram of FIG. 2. The first step is to perform two calibrations for different material pairs under the exactly same system conditions.

The first calibration is to obtain a pair of numerical relationships for the front detector at the high energy level H and the low energy value L for two materials c and S, where c denotes the material having an x-ray attenuation coefficient as a function of x-ray energy $\mu_c(E)$ the same as that of microcalcification deposits, and s denotes the material having an x-ray attenuation coefficient as a function of x-ray energy $\mu_s(E)$ that same as that of an average tissue substance. An average breast soft tissue composition can be chosen as having 50% fat tissue and 50% lean tissue. When using other values of fat and lean tissue composition, the present invention holds equally true. The following is a description of how to perform dual-energy calibration for true tissue components.

Dual-energy calibration methods are described in detail in the Chao disclosures. In the present invention, it is required that the calibration be conducted regarding the actual material composition that exists in the human breasts. For conducting calibration measurements, according to the methods described in the Chao disclosures, a number of material plates of the two composition materials should be used in the calibration measurements. Currently, such standard tissue samples have not been available. The present invention provides an improved dual-energy calibration method that can use another pair of materials for calibration measurements to obtain the accurate calibration data for the desired different material pair. The scientific foundation of the improved calibration method is described below:

Assume that it is desired to obtain numerical equations for the calibration data material pair of (p,q), but the direct material (p,q) data is not available due to certain practical limitations. On the other hand, another material pair (u,v) is available for use in the calibration measurements. Also, all of the x-ray attenuation coefficients as x-ray energy functions $\mu_u(E)$, $\mu_v(E)$, $\mu_p(E)$ and $\mu_q(E)$ are known. In mammography, for one type of calibration, such a (p,q) material pair can be, for example, glandular tissue and adipose tissue in the human breast. The (u,v) material pair can be, for example, a pair of commercially available materials, such polyethylene ($CH_2$) sheet and water ($H_2O$). For another type of calibration, such a (p,q) material pair can be calcification and soft tissue in the human breast. Then the (u,v) material pair can be, for example, a pair of commercially available materials, such as aluminum (Al) and a plastic material, Lucite™. The dual-energy equation system is written as $$D_{fPHh}(x, y) = \int [\Phi_{0H}(E) \times \exp(-(\mu_u(E) \times u(x, y) + \mu_v(E) \times v(x, y))] \times S_f(E) dE \quad (1a)$$

and $$D_{fPLh}(x, y) = \int [\Phi_{0L}(E) \times \exp(-(\mu_u(E) \times u(x, y) + \mu_v(E) \times v(x, y))] \times S_f(E) dE \quad (1b)$$

where $\Phi_{0H}(E)$ and $\Phi_{0L}(E)$ are the energy spectra of the x-ray source 14 at the higher energy level H and the lower energy level L, respectively. The projection mass densities u(x,y) and v(x,y) are in units of gram/centimeter$^2$ (g/cm$^2$). The mass attenuation coefficients $\mu_u(E)$ and $\mu_v(E)$ are expressed in units of centimeter$^2$/gram (cm$^2$/g). All of these values are known. $S_f(E)$ is the x-ray spectral sensitivity of the front detector.

Conduct functional decomposition for the energy-dependent attenuation coefficient function $\mu_u(E)$ $$\mu_u(E) = u_p \times \mu_p(E) + u_q \times \mu_q(E) \quad (2a)$$

where the constants up and uq can be obtained through standard least-square data fitting methods. Similarly $$\mu_v(E) = v_p \times \mu_p(E) + v_q \times \mu_q(E) \quad (2b)$$

where the constant values $u_p$ and $u_q$ can be obtained through standard least-square data fitting methods.

It should be noted that such functional decomposition cannot be generally true from a mathematics point of view. However, it has been established through extensive analysis of experimental data that for substances composed of chemical elements with low to medium atomic number Z, such as chemical elements carbon, hydrogen, oxygen, nitrogen, up to calcium, as in the human body, and as long as the x-ray energy is within the medical diagnostic energy range, such as between 20 keV and 150 keV, a third x-ray mass attenuation function can always be written as a sum of two other x-ray mass attenuation functions with good approximation. The energy-dependent attenuation function in the exponent of the exp( ) of equations (1a) and (1b) is denoted UF(E):

$$-UF(E) = \mu_u(E) \times u(x,y) + \mu_v(E) \times v(x,y) \quad (3)$$
$$= [u(x,y) \times u_p + v(x,y) \times v_p] \times \mu_p(E) +$$
$$[u(x,y) \times u_q + v(x,y) \times v_q] \times \mu_q(E)$$

When $$u(x,y) \times u_p + v(x,y) \times v_p \equiv p(x,y) \quad (4a)$$

and $$u(x,y) \times u_q + v(x,y) \times v_q \equiv q(x,y) \quad (4b)$$

where the symbol "≡" represents definition, then $$-UF(E) = \mu_p(E) \times p(x,y) + \mu_q(E) \times q(x,y) \quad (5)$$

Therefore, the procedure for the improved calibration includes the following steps:

(1) Conduct calibration measurements by using the (u,v) material pair as described in the Chao disclosures. As a result, this numerical equation system is obtained:

$$D_H = D_{DH}[u,v] \quad (6a)$$
$$D_L = D_{DL}[u,v] \quad (6b)$$

(2) Conduct functional decomposition for the energy dependent attenuation coefficient functions $\mu_u(E)$ and $\mu_v(E)$ $$\mu_u(E) = u_p \times \mu_p(E) + u_q \times \mu_q(E) \quad (7a)$$
$$\mu_v(E) = v_p \times \mu_p(E) + v_q \times \mu_q(E) \quad (7b)$$

by using standard least-square data fitting methods, and obtain the constants $u_p$, $u_q$, $v_p$, and $v_q$.

(3) For each data pair (u,v) in equations (6a),(6b), calculate $$u \times u_p + v \times v_p = p \quad (8a)$$
$$u \times u_q + v \times v_q = q \quad (8b)$$

and obtain a new dual-energy numerical equation system $$D_H = D_{DH}[p,q] \quad (9a)$$
$$D_L = D_{DL}[p,q] \quad (9b)$$

(4) Solve the equation system $D_H = D_{DH}[p,q]$ and $D_L = D_{DL}[p,q]$ for the variable pair (p,q) as a function of the variable pair ($D_H$,$D_L$) through numeric inversion and obtain $$p = p[D_H, D_L] \quad (10a)$$
$$q = q[D_H, D_L] \quad (10b)$$

For performing two types of dual-energy decomposition, two corresponding types of calibration are conducted. The first type of calibration is for the material pair (c,s) for microcalcification and soft tissue in the human breast. By using the above-described calibration procedures, a pair of quantitative explicit numerical functions $$D_H = D_{DH}[c,s] \quad (11a)$$
$$D_L = D_{DL}[c,s] \quad (11b)$$

are established, where the notations $D_H[\ ]$ and $D_L[\ ]$ represent functional relationships with c and s as variables. The equation system is solved by, for example, numerical inversion to obtain a numerical equation system $$c = c[D_H, D_L] \quad (12a)$$
$$s = s[D_H, D_L] \quad (12b)$$

This numerical equation system is applicable to all normalized pixels. From the measured signal pair ($D_H$,$D_L$) for any pixel, the material composition data pair c and s for that pixel can be readily found.

The second type of calibration is to obtain a pair of numerical relationships for the front detector at the high energy level H and the low energy value L for two materials f and g, where f denotes the material having an x-ray attenuation coefficient $\mu_f(E)$ the same as that of fat tissue, and g denotes the material having an x-ray attenuation coefficient $\mu_g(E)$ the same as that of lean tissue. Thus, the quantitative explicit functions $$D_H = D_{DH}[f,g] \quad (13a)$$
$$D_L = D_{DL}[f,g] \quad (13b)$$

are established. The equation systems is solved by, for example, numerical inversion to obtain a numerical equation system $$f = f[D_H, D_L] \quad (14a)$$
$$g = g[D_H, D_L] \quad (14b)$$

This numerical equation system is applicable to all normalized pixels. From the measured signal pair ($D_H$,$D_L$), the material composition data pair (f,g) can be readily found.

To avoid misunderstanding, two points need to be mentioned. First, for better accuracy, the calibration materials should be chosen to have a composition as close as possible to the actual tissue compositions in terms of x-ray interaction. This should be clear based on general error theory for experimental measurements. For example, when $\mu_u(E)$ is close to $\mu_p(E)$, and $\mu_v(E)$ is close to $\mu_q(E)$, the error due to transformation of (7a) and (7b) is smaller.

The second point is that there exists a number of trivial alternatives of the order of the calculation steps. For example, after step (1), conducting calibration measurements by using the (u,v) material pair and establishing the numerical relationships (6a) and (6b), instead of performing a material pair transformation (8a) and (8b) to obtain the numerical relationships (9a) and (9b), one can directly conduct the inversion for the (6a) and (6b) to obtain $$u = u[D_H, D_L] \quad (15a)$$
$$v = v[D_H, D_L] \quad (15b)$$

Then, applying the relationships (15a) and (15b) to the image data, $D_{fPHh}(x,y)$ and $D_{fPLh}(x,y)$, two material images u(x,y) and v(x,y) can be obtained. After that, by using the equations (8a) and (8b)

$$p(x,y) = u(x,y) \times u_p + v(x,y) \times v_p \quad (16a)$$
$$q(x,y) = u(x,y) \times u_q + v(x,y) \times v_q \quad (16b)$$

the entire images u(x,y) and v(x,y) are transformed, point by point, into two images p(x,y) and q(x,y). This is only a trivial variation of the order for mathematical calculations without any essential change of the method. Therefore, it is contemplated that the procedures as described in equations (1a),(1b) through (12a),(12b) include these and other similar trivial alternatives.

The second step of the method of the present invention is to acquire a pair of high-spatial-resolution composite images of the front detector $D_{fHh}(x,y)$ and $D_{fLh}(x,y)$, where the subscript f denotes an image of the front detector 16, subscript H denotes a high-energy-level image, subscript L denotes a low-energy-level image, subscript h denotes a high-resolution image, and (x,y) denotes the two-dimensional Cartesian coordinates of a detector cell of the front detector 16. Each of the images in image data pair $D_{fHh}(x,y)$ and $D_{fLh}(x,y)$ contains a scatter component and a primary x-ray component. The primary x-ray component contains a fat tissue component, a lean tissue component, and a microcalcification component.

The third step is to separate each image of the image air $D_{fHh}(x,y)$ and $D_{fLh}(x,y)$ into the scatter component and primary x-ray component. This is done through a number of data acquisition and calculation steps, as described in the above-identified U.S. patents, to calculate a pair of high-spatial-resolution scatter-only images at the front detector $D_{fSHh}(x,y)$ and $D_{fSLh}(x,y)$, where the subscript S denotes that this is a scatter-only image. This step is the same as the corresponding step in the previously-identified patents.

The fourth step is to calculate the high-spatial-resolution primary x-ray image pair $D_{fPHh}(x,y)$ and $D_{fPLh}(x,y)$ from the equations $$D_{fPHh}(x,y) = D_{fHh}(x,y) - D_{fSHh}(x,y) \quad (17a)$$

$$D_{fPLh}(x,y) = D_{fLh}(x,y) - D_{fSLh}(x,y) \quad (17b)$$

where the subscript P denotes that this image is composed only of primary x-rays. This step is also the same as described in the U.S. patents.

The fifth step is to perform a dual-energy decomposition for the image pair $D_{fPHh}(x,y)$ and $D_{fPLh}(x,y)$ by using the calibrated numerical equation system (12a),(12b). As a result, two material composition images $c_1(x,y)$ and $s_1(x,y)$ are obtained. In this image pair, $c_1(x,y)$ is basically a microcalcification image and $s_1(x,y)$ is basically an average soft tissue image of the breast.

The sixth and final step is to perform a dual-energy decomposition for the image pair $D_{fPHh}(x,y)$ and $D_{fPLh}(x,y)$ by using the calibrated numerical equation system (14a), (14b). As a result, two material composition images $f_1(x,y)$ and $g_1(x,y)$ are obtained. In this image pair, $f_1(x,y)$ is basically a fat tissue image and $g_1(x,y)$ is basically a lean tissue image of the breast. However, both $f_1(x,y)$ and $g_1(x,y)$ contain microcalcification information, which has not been explicitly specified and appropriately quantified.

At this point, usable results have been obtained by the decomposition of a single breast image into five component images: the scatter image $D_{fs}(x,y)$, the microcalcification image $c_1(x,y)$, the average mixed tissue image $s_1(x,y)$, the fat tissue image $b_1(x,y)$, and the lean tissue image $g_1(x,y)$. Using these component images, information needed to make a diagnosis is significantly enhanced over that of the prior art.

However, the power of dual-energy decomposition has not yet been fully exploited. The above results may be considered as a good first approximation for breast imaging data. The reason that these component images can only be considered as first approximation is because that, in performing the above procedures of dual-energy decomposition, the breast is assumed to be composed of only two materials. A real breast is composed of three materials.

Second Order Approximation

The next part of the present specification describes a method of second order approximation for taking into account the three material components of a human breast. First, the scientific principles are explained, and then the steps of the method are described.

In a human breast, there are basically three significant material compositions: adipose tissue, which can be represented by a fat tissue, glandular duct tissue, which can be represented by a lean tissue, and microcalcification deposits, which contain calcium. Decomposition of a system into three independent material components is generally beyond the capability of dual-energy imaging method. If there existed a triple-energy decomposition method, performing data acquisition at three different energy levels, then three material compositions could be independently separated. However, there currently is no triple-energy decomposition method.

The following explains how to use the dual-energy method to approximately separate the three material components of a human breast. This is possible because there are special conditions of the human breast that can be utilized to achieve a good approximation. The first special condition is that the x-ray attenuation of fat tissue and lean tissue in the breast tissue are very close when compared to that of the microcalcification. The second condition is that microcalcification deposits in the human breast are generally limited to existing in small, isolated regions, and in many cases, to be within only few single image pixels.

The dual-energy imaging equation of the breast can be represented by the equation pair $$D_{fPHf}(x, y) = \int [\Phi_{0H}(E) \times \exp(-(\mu_c(E) \times c(x, y) + \mu_f(E) \times f(x, y) + \mu_g(E) \times g(x, y))] \times S_f(E)dE \quad (18a)$$

and $$D_{fPLh}(x, y) = \int [\Phi_{0L}(E) \times \exp(-(\mu_c(E) \times c(x, y) + \mu_f(E) \times f(x, y) + \mu_g(E) \times g(x, y))] \times S_f(E)dE \quad (18b)$$

The projection mass densities c(x,y), f(x,y), and g(x,y) of the subject are in units of gram/centimeter$^2$ (g/cm$^2$). The mass attenuation coefficients $\mu_c(E)$, $\mu_f(E)$, and $\mu_g(E)$ are known and expressed in units of centimeter$^2$/gram (cm$^2$/g). The energy-dependent exponent of the exponential function exp( ) in equation system (18a), (18b) is denoted as AF(E), and is $$-AF(E) = \mu_c(E) \times c(x, y) + \mu_f(E) \times f(x, y) + \mu_g(E) \times g(x, y) \quad (19)$$

There are three independent mass attenuation functions $\mu_c(E)$, $\mu_f(E)$, and $\mu_g(E)$ connected by three unknown parameters for material density values c(x,y), f(x,y), and g(x,y). Dual-energy measurements only provide two measured signals $D_{fPHh}(x,y)$ and $D_{fPLh}(x,y)$, from which only two unknown parameters can be determined.

The basic method used for quantitative evaluation of each tissue component is a method of function decomposition. One energy-dependent mass attenuation function must be expressed as a sum of the other two functions. For example, to perform a basic dual-energy decomposition for fat tissue and lean tissue, the calcium function $\mu_c(E)$ is decomposed as $$\mu_c(E) = R_{cf} \times \mu_f(E) + R_{cg} \times \mu_g(E) \quad (20)$$

where $R_{cf}$ and $R_{cg}$ are constants. Note that for the human body system, where the x-ray energy is within medical diagnostic energy range, the third x-ray mass attenuation function can always be written as a sum of other two x-ray mass attenuation functions with good approximation. The exact values of $R_{cf}$ and $R_{cg}$ can be calculated by using standard least-square data fitting methods. For example, within an x-ray energy range of 16 keV and 100 keV, by applying least-square data fitting methods to equation (20), it can be found that $R_{cf}=-34$ and $R_{cg}=+33$. Accurate values of the $R_{cf}$ and $R_{cg}$ are dependent on the x-ray energy range used in the hardware system.

Some general observations can be made regarding the parameter pair $R_{cf}$ and $R_{cg}$. First, $R_{cg}$ is always positive, and $R_{cf}$ is always negative. Secondly, the absolute values of $R_{cf}$ and $R_{cg}$ are always rather large and are always close to each other. For example, for the diagnostic energy range, the absolute value of $R_{cf}$ and $R_{cg}$ can be assumed to be between 10 to 50. The underlying physical reason for these two characteristic features comes from the fact that calcium has a much larger attenuation coefficient at lower energy than both fat tissue and lean tissue, and at the low energy, the lean tissue has a slightly larger attenuation coefficient than that of fat. These characteristic features produce very uncommon results in the decomposed component x-ray images: when the image is decomposed into fat tissue and lean tissue component images, each microcalcification point produces a positive high-intensity attenuation change in the lean tissue image at that point, each microcalcification point produces a negative high-intensity attenuation change in the fat tissue image at that point, and these positive and negative points have an exact quantitative relationship. For example, one microgram of microcalcification produces a positive attenuation change corresponding to approximately 30 micrograms of lean tissue intensity change, and one microgram of microcalcification produces a negative attenuation point corresponding to approximately 30 micrograms of fat tissue intensity change. These characteristic features are utilized in the present invention for quantitatively separating the superimposed microcalcification image from the lean tissue image and from the fat tissue image.

AF(E) can be again written in a form that contains only two basis functions $$-AF(E) = \mu_f(E) \times [f(x, y) + R_{cf} \times c(x, y)] + \mu_g(E) \times [g(x, y) + R_{cg} \times c(x, y)] \quad (21)$$

or $$-AF(E)=\mu_f(E) \times fc(x,y) + \mu_g(E) \times gc(x,y) \quad (22)$$

where $$fc(x,y)=f(x,y)+R_{cf} \times c(x,y) \quad (23a)$$

$$gc(x,y)=g(x,y)+R_{cg} \times c(x,y) \quad (23b)$$

Because AF(E) contains only two independent functions $\mu_f(E)$ and $\mu_g(E)$, by using dual energy decomposition procedures as described in the Chao disclosures, two unique energy-independent parameters can be obtained through solving equation system (18a) and (18b), the solution pair is fc(x,y) and gc(x,y). Note that the solution pair fc(x,y) and gc(x,y) are exactly the solution pair of the first approximation. That is $$f_1(x,y)=fc(x,y)=f(x,y)+R_{cf} \times c(x,y) \quad (24a)$$

$$g_1(x,y)=gc(x,y)=g(x,y)+R_{cg} \times c(x,y) \quad (24b)$$

After performing dual-energy decomposition according to the procedures of the first order approximation, the third material component is projected and superimposed onto the two basis component images as expressed in (24a) and (24b), as $R_{cf} \times c(x,y)$ on the fat tissue image and as $R_{cg} \times c(x,y)$ on the lean tissue image. Generally speaking, the portion of superimposed third component image cannot be separated from the two component images because what can be calculated by using dual-energy decomposition are only fc(x,y) and gc(x,y).

The present invention utilizes certain characteristic specific conditions for human breast imaging to approximately separate the third material composition. It is known that, in the human breast, the microcalcification deposits are limited to existing in small regions. For a small region, the soft tissue density can be assumed to change approximately smoothly. The following is a outline of the basic steps of separating microcalcification image spots from the soft tissue image. First, identify the microcalcification spots on the image. The microcalcification spots must be (a) a positive signal/negative signal pair, each having approximately equal absolute values of amplitude, but having opposite signs, and (b) superimposed at exactly the same corresponding locations on the lean tissue image and the fat tissue image. Second, interpolated an image intensity from nearby surrounding soft tissue pixels to replace the image intensity of these suspected microcalcification spots. Third, subtract the interpolated signal intensity from the original signal intensity gc(x,y) and fc(x,y) at the identified spot to determine if the intensity change is consistent with that predicted by decomposition equation (20) for the microcalcification function. If the microcalcification intensity on the two soft tissue images are quantitatively consistent with that predicted by the equation (20), the spot meets the preliminary test for a microcalcification spot. In addition to this preliminary test, there is a further test, to be described below.

The following is a description of the scientific foundation of how to obtain pure microcalcification single component image through the second decomposition.

In the second decomposition at the accuracy level of first order approximation, the two basis functions are chosen to be $\mu_c(E)$ and $\mu_{sa}(E)$, where $\mu_c(E)$ is the energy-dependent attenuation function for microcalcification and $\mu_{sa}(E)$ is the attenuation function for an average soft tissue composition. Two images $c_1(x,y)$ and $s_1(x,y)$ are obtained as a result of the second decomposition at an accuracy level of first order approximation. In the first order approximation, the breast was assumed to have only two material compositions with the mass attenuation coefficient functions $\mu_c(E)$ and $\mu_{sa}(E)$. According to the actual breast material composition, the energy-dependent exponent in the equations (18a) and (18b) is denoted as BF(E):

$$-BF(E) = \mu_c(E) \times c(x, y) + \mu_f(E) \times f(x, y) + \mu_g(E) \times g(x, y) \quad (25)$$

or $$-BF(E) = \mu_c(E) \times c(x, y) + \mu_{sa}(E) \times s_a(x, y) + \delta\mu_s(E) \times \delta s(x, y) \quad (26)$$

where the average tissue mass attenuation coefficient function $\mu_{sa}(E)=50\% \ \mu_f(E)+50\% \ \mu_g(E)$. $\delta\mu_s(E) \times \delta s(x,y)$ is the local deviation at the pixel (x,y) from the averaged soft tissue attenuation $\mu_{sa}(E) \times s_a(x,y)$. For example, when the tissue composition at (x,y) is exactly 50% fat tissue and 50% lean tissue, then $\delta\mu_s(E)=0$. Otherwise, for performing dual-energy decomposition according to the basis function $\mu_c(E)$ and $\mu_{sa}(E)$, the energy dependent function $\delta\mu_s(E)$ must be decomposed into two basis functions $\mu_c(E)$ and $\mu_{sa}(E)$ as $$\delta\mu_s(E)=R_{sc}\times\mu_c(E)+R_{ss}\times\mu_{sa}(E) \tag{27}$$

where $R_{sc}$ and $R_{ss}$ are two constants, the exact values of which can be calculated by using standard least-square data fitting methods, when the local tissue composition is known. Then, $$-BF(E) = \mu_{sa}(E)\times[s_a(x,y)+R_{ss}\times\delta s(x,y)] + \tag{28}$$
$$\mu_c(E)\times[c(x,y)+R_{sc}\times\delta s(x,y)]$$

or $$-BF(E)=\mu_c(E)\times cs(x,y)+\mu_{sa}(E)\times ss(x,y) \tag{29}$$

where $$cs(x,y)=c(x,y)+R_{sc}\times\delta s(x,y) \tag{30a}$$

and $$ss(x,y)=s_a(x,y)+R_{ss}\times\delta s(x,y) \tag{30b}$$

Some general observations can be made regarding the parameter pair $R_{ss}$ and $R_{sc}$. First, $R_{ss}$ is not much different from 1.0 and $R_{sc}$ is much smaller than 1.0. The underlying physical reason stems from the fact that the energy-dependent behavior of the function $\delta\mu_s(E)$ is not much different from that of the average tissue function $\mu_{sa}(E)$, and very much different from that of $\mu_c(E)$.

Note that the dual-energy decomposition results obtained at the accuracy level of the first order approximation $c_1(x,y)$ is exactly $cs(x,y)$ and that $s_1(x,y)$ is exactly $ss(x,y)$. That is, $$c_1(x,y)=cs(x,y)=c(x,y)+R_{sc}\times\delta s(x,y) \tag{31a}$$

$$s_1(x,y)=ss(x,y)=s_a(x,y)+R_{ss}\times\delta s(x,y) \tag{31b}$$

Therefore, because of the local deviation of the actual tissue composition from the assumed average tissue composition, the microcalcification image $c_1(x,y)$ obtained through the first order approximation is composed of two images. One is the true microcalcification image $c(x,y)$, and the other image is produced by local deviation of the tissue composition from the assumed average composition. The exact signal intensity of the superimposed image is $R_{sc}\times\delta s(x,y)$. Generally speaking, such superimposed images due to the existence of a third material cannot be separated by using the dual-energy method. However, based on utilizing some specific conditions for the human breast, the present invention provides approximation methods for removing the effects of the third material $R_{sc}\times\delta s(x,y)$ on the true microcalcification image $c(x,y)$.

For separating the third material effects on the microcalcification image, two characteristic feature differences between the image $R_{sc}\times\delta s(x,y)$ and that of image $c(x,y)$ are utilized: (a) the local deviation of soft tissue composition from the average composition $R_{sc}\times\delta s(x,y)$ has a smooth spatial distribution, in a way similar to that of the soft tissue spatial distribution $sa(x,y)$, while the microcalcification image has an abrupt intensity change at certain small regions; and (b) the amplitude of deviation image $R_{sc}\times\delta s(x,y)$ is small, because, as mentioned above, $R_{sc}$ is small.

Figure 3:
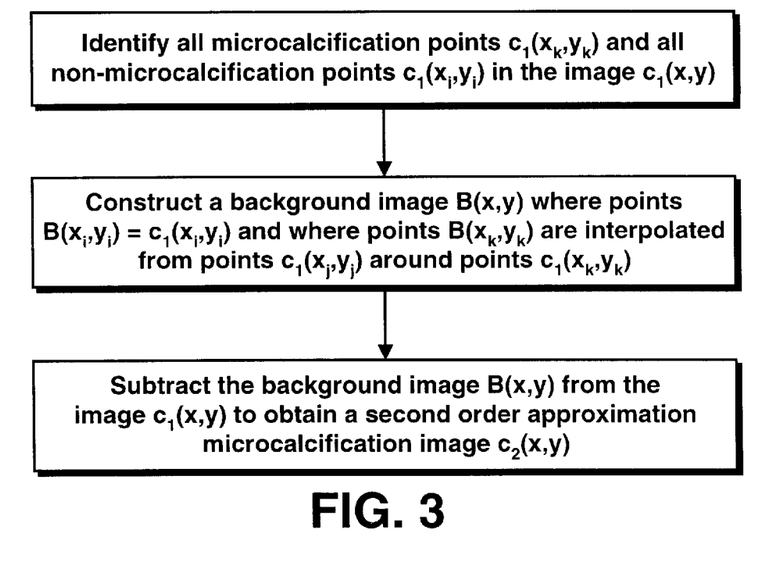
FIG. 3 is a flow diagram of the method for obtaining a relatively pure microcalcification image.

FIG. 3 and the following describe the procedure for obtaining a pure microcalcification image at an accuracy level of the second order approximation from the second decomposition.

(1) In the microcalcification image $c_1(x,y)$, first identify all the microcalcification points $(x_k,y_k)$. The microcalcification points are prominently different from other image points because the microcalcification image $c_1(x,y)$ is composed essentially of high-intensity isolated image points presented on a smoothly changing background. The microcalcification points are identified by pixels with a sudden intensity change at isolated points. Sometimes, microcalcification can take the form of clusters, so the points are not always individually isolated. The present invention contemplates that such clusters containing a small number of microcalcification points with a signal intensity much higher than those of adjacent points exist.

(2) Construct a background image $B(x,y)$ for $c_1(x,y)$ from pixels $(x_i,y_i)\neq(x_k,y_k)$. That is, background image $B(x_i,y_i)=c_1(x_i,y_i)$ for $x_i\neq x_k$ and $y_i\neq y_k$ for all the non-microcalcification points. The signals in $B(x_i,y_i)$ have excluded the microcalcification points, so they must be produced by local tissue composition deviation, hence are microcalcification background signals.

(3) In the background image $B(x,y)$ for those pixels $(x_k,y_k)$ that have been identified as microcalcification points, the signal intensity is assumed to be equal to an averaged signal intensity value interpolated from the signal intensity of the surrounding pixels. That is, $$B(x_k,y_k)=\text{averaged}[c_1(x_j,y_j)] \tag{32}$$

for j around k. Because the tissue composition has a relatively smooth change in comparison with that of the microcalcification deposits, the averaged $c_1(x_j,y_j)$ will be very close to the actual tissue composition variation at the point $(x_k,y_k)$.

(4) Subtract the tissue background image $B(x,y)$ from the first approximation microcalcification image $c_1(x,y)$ to obtain the second order approximation microcalcification image $$c_2(x,y)=c_1(x,y)-B(x,y) \tag{33}$$

In the image $c_2(x,y)$, the image signal intensity should accurately represent quantitative microcalcification density without being affected by tissue composition variations.

Figure 4:
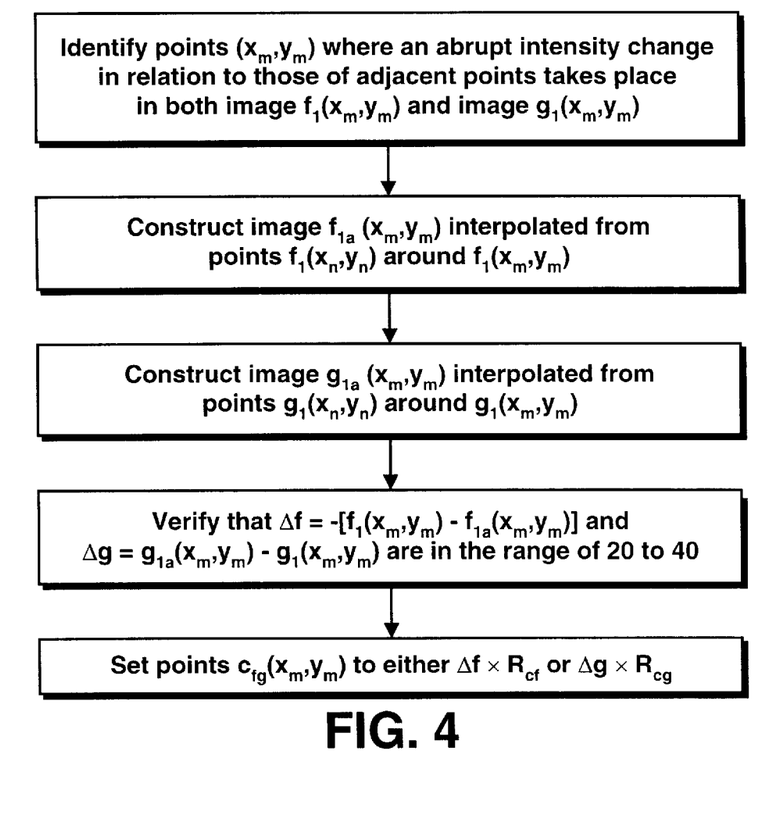
FIG. 4 is a flow diagram of the method for obtaining a microcalcification image based on the information provided by the fat and lean tissue images.

The steps for construction of a microcalcification image $c_{fg}(x,y)$ based on the information in the first order approximation fat and lean tissue images $f_1(x,y)$ and $g_1(x,y)$ are described in FIG. 4 and are as follows:

(1) Identify those points $(x_m,y_m)$ where an abrupt intensity change in relation to those of adjacent points takes place simultaneously in the fat tissue image $f_1(x,y)$ and the lean tissue image $g_1(x,y)$. The points $(x_m,y_m)$ are suspected calcification sites as given by the tissue images $f_1(x,y)$ and $g_1(x,y)$.

(2) Verify whether the abrupt signal change at each point $(x_m,y_m)$ is consistent with that predicted. Only when the predicted signal change on the fat tissue image $f_1(x,y)$ and lean tissue image $g_1(x,y)$ can both be quantitatively confirmed is the new microcalcification image signal $c_{fg}(x,y)$ constructed. To do this, first calculate a pair of interpolated signal intensities $f_{1a}(x_m,y_m)$ and $g_{1a}(x_{m,ym})$, so that $f_{1a}(x_m,y_m)=\text{averaged}[f_1(x_n,y_n)]$ for n around m, and $g_{1a}(x_m,y_m)=\text{averaged}[g_1(x_{n,yn})]$ for n around m. Then calculate $$\Delta f=-[f_1(x_m,y_m)-f_{1a}(x_m,y_m)] \tag{34}$$

and $$\Delta g = g_{1a}(x_m, y_m) - g_1(x_m, y_m) \quad (35)$$

When these two quantities are close to being within a certain range, for example, between 20 to 40, the microcalcification at the pixel $(x_m, y_m)$ is confirmed. When $\Delta f$ and $\Delta g$ are not quantitatively consistent, the most probable reasons are that (a) the point selected according to the criteria of abrupt intensity change is not a calcification deposit, but actually represents some peculiar soft tissue structure, or (b) the point could contain calcification, but the signal intensity of the calcification is too low and submerged in noise. In both cases, the selected point cannot be taken as a calcification deposit, and should be excluded from the calcification image according to the information provided by the fat tissue image $f_1(x,y)$ and lean image $g_1(x,y)$. Thus, the calcification image $c_{fg}(x,y)$ may not be entirely identical to the calcification image $c_2(x,y)$. Even with these possible slight differences between the two calcification images obtained from different data analysis methods, both $c_2(x,y)$ and $c_{fg}(x,y)$ provide their own reference data. Both images are useful.

(3) According to the results of step (2), let $$c_{fg}(x_m, y_m) = -[f_2(x_m, y_m) - f_1(x_m, y_m)] \times R_{cf} \quad (36)$$

or $$c_{fg}(x_m, y_m) = [g_2(x_m, y_m) - g_1(x_m, y_m)] \times R_{cg} \quad (37)$$

Either value of equations (36) or (37) can be used as the calcification image intensity, because these values are close to each other. Choosing one as the final result is largely a matter of operator preference and depends on the operator's judgement. If a further comparison is needed, the value of equation (36) may be better than that of equation (37) because, generally, the signal intensity of fat tissue in the breast has a smoother distribution than that of lean tissue. Consequently, the interpolated and averaged value may be more accurate.

Figure 5:
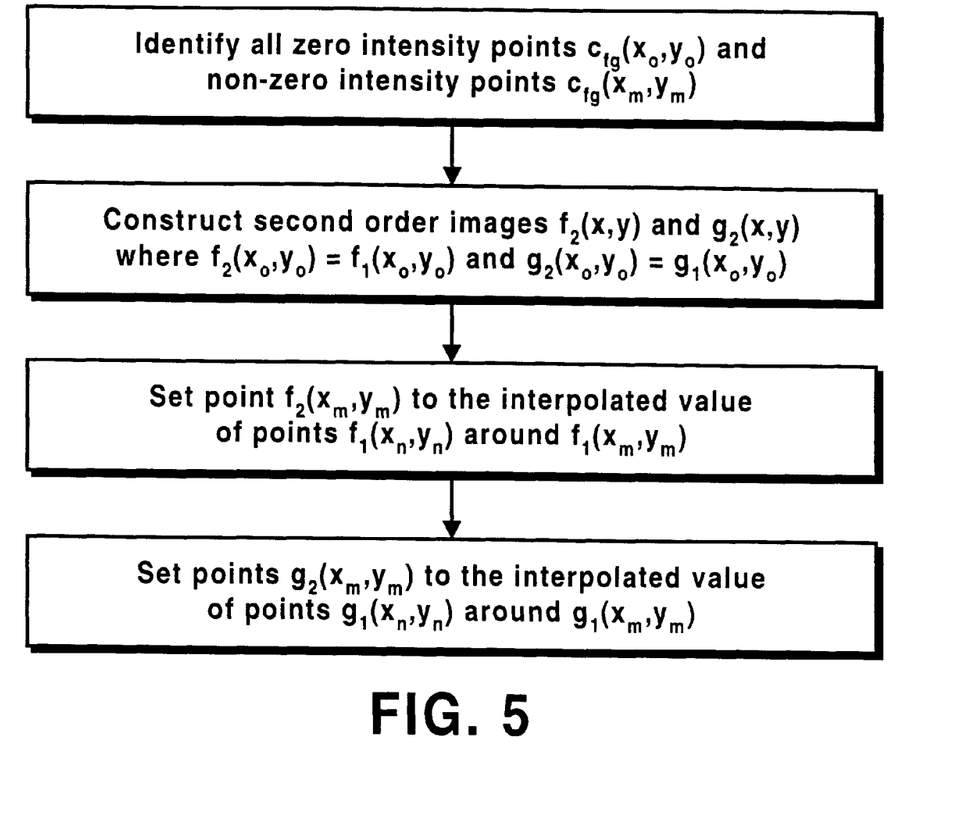
FIG. 5 is a flow diagram of the method for further correction of the fat tissue and lean tissue images.

The steps for obtaining a second order approximation of the fat tissue image $f_2(x,y)$ and lean tissue image $g_2(x,y)$ in which the microcalcification image is removed are described in FIG. 5 and are as follows:

(1) For each pixel of the second order microcalcification image $c_{fg}(x,y)$, identify those points $c_{fg}(x_o, y_o)$ whose intensity is zero and those points $c_{fg}(x_m, y_m)$ whose intensity is not zero.

(2) Construct images $f_2(x,y)$ and $g_2(x,y)$, where there are no changes between the first order and second order images at the zero intensity points, that is, $f_2(x_o, y_o) = f_1(x_o, y_o)$ and $g_2(x_o, y_o) = g_1(x_o, y_o)$ (3) Set the remainder of the points $f_2(x_m, y_m)$ and $g_2(x_m, y_m)$ to the average of the signal intensity of the points in the vicinity, that is, $f_2(x_m, y_m) = \text{averaged}[f_1(x_n, y_n)]$ for n around m and $g_2(x_m, y_m) = \text{averaged}[g_1(x_n, y_n)]$ for n around m. After going over all pixels (x,y), two corrected tissue images $f_2(x,y)$ and $g_2(x,y)$ are obtained with microcalcification effects corrected.

Thus it has been shown and described a method of digital mammography which satisfies the objects set forth above.

Since certain changes may be made in the present disclosure without departing from the scope of the present invention, it is intended that all matter described in the foregoing specification and shown in the accompanying drawings be interpreted as illustrative and not in a limiting sense.

What is claimed is:

1. A method for performing dual-energy x-ray imaging of a human breast using an imaging system having two-dimensional x-ray detectors, said subject being composed substantially of fat tissue f, lean tissue g, and microcalcification material c, that interact differently with x-rays, said fat tissue and lean tissue combining as an average soft tissue s, said imaging system including, in physical sequence from front to back, a dual-energy x-ray source, a front two-dimensional x-ray detector having a plurality of front detection locations identified by the notation (x,y), a beam selection means, and a rear two-dimensional x-ray detector having a plurality of selected rear detection locations identified by the notation (i,j), said subject being between said x-ray source and said front detector, said x-ray source being adapted to emit x-rays at two different average energy levels, H and L, for passage through said subject, said x-rays including primary x-rays having their direction of travel unaltered by interaction with said subject and said x-rays including scatter x-rays having their direction of travel altered by interaction with said subject, said beam selection means permitting said rear detector to receive a passed portion of said x-rays and preventing said rear detector from receiving a blocked portion of said x-rays, said front detector having selected detection locations, identified by the notation (x(i),y(j)), that are intersected by x-ray projection lines extending from said x-ray source to said selected rear detection locations (i,j), said method comprising the steps of:

(a) performing a first calibration to obtain a pair of numerical relationships for said front detector at said high energy and said low energy for said microcalcification c and said soft tissue s to obtain the functions $c = c[D_H, D_L]$ and $s = s[D_H, D_L]$;

(b) performing a second calibration to obtain a pair of numerical relationships for said front detector at said high energy and said low energy for said fat tissue f and said lean tissue g to obtain the functions $f = f[D_H, D_L]$ and $g = g[D_H, D_L]$;

(c) illuminating said subject with x-rays of said average energy level H;

(d) acquiring a high-resolution image $D_{fHh}(x,y)$ from said front detection locations (x,y), said image $D_{fHh}(x,y)$ being composed of said primary x-rays and said scatter x-rays;

(e) illuminating said subject with x-rays of said average energy level L;

(f) acquiring a high-resolution image $D_{fLh}(x,y)$ from said front detection locations (x,y), said image $D_{fLh}(x,y)$ being composed of said primary x-rays and said scatter x-rays;

(g) calculating a pair of high-resolution scatter x-ray images $D_{fSHh}(x,y)$ and $D_{fSLh}(x,y)$;

(h) calculating a pair of high-resolution primary x-ray images $D_{fPHh}(x,y) = D_{fHh}(x,y) - D_{fSHh}(x,y)$ and $D_{fPLh}(x,y) = D_{fLh}(x,y) - D_{fSLh}(x,y)$;

(i) performing a dual-energy decomposition for said image pair $D_{fPHh}(x,y)$ and $D_{fPLh}(x,y)$ using said functions $c = c[D_H, D_L]$ and $s = s[D_H, D_L]$ to obtain two first order approximation material composition images $c_1(x,y)$ and $s_1(x,y)$; and (j) performing a dual-energy decomposition for said image pair $D_{fPHh}(x,y)$ and $D_{fPLh}(x,y)$ using said functions $f = f[D_H, D_L]$ and $g = g[D_H, D_L]$ to obtain two first order approximation material composition images $f_1(x,y)$ and $g_1(x,y)$;

(k) whereby said breast image is decomposed into five components, said scatter x-ray image pair $D_{fSHh}(x,y)$, $D_{fSLh}(x,y)$, said first order approximation microcalcification image $c_1(x,y)$, said first order approximation soft tissue image $s_1(x,y)$, said first order approximation fat tissue image $f_1(x,y)$, and said first order approximation lean tissue image $g_1(x,y)$.

2. The method for performing dual-energy x-ray imaging of a human breast of claim 1 wherein:

(a) a general calibration method comprises the steps of (1) determining a dual-energy equation system for two known materials u and v having known x-ray mass attenuation functions $\mu_u(E)$ and $\mu_v(E)$ as $D_H=D_H[u,v]$, $D_L=D_L[u,v]$, (2) conducting functional decomposition for energy-dependent attenuation coefficient functions $\mu_u(E)=u_p\times\mu_p(E)+u_q\times\mu_q(E)$ and $\mu_v(E)=v_p\times\mu_p(E)+v_q\times\mu_q(E)$ using standard least-square data fitting methods to obtain constants $u_p$, $u_q$, $v_p$, and $v_q$, (3) calculating $u\times u_p+v\times v_p=p$, and $u\times u_q+v\times v_q=q$ for each coordinate pair (u,v) to obtain dual-energy equation system $D_H=D_H[p,q]$, $D_L=D_L[p,q]$, and (4) solving said equation system $D_H=D_H[p,q]$, $D_L=D_L[p,q]$ for materials p and q with known x-ray mass attenuation functions $\mu_p(E)$ and $\mu_q(E)$ as a function of variable pair $(D_H,D_L)$ through numerical inversion to obtain an equation system $p=p[D_H,D_L]$ and $q=q[D_H,D_L]$;

(b) said first calibration includes substituting said microcalcification material c and said composite tissue s for said materials p and q in said general calibration method to obtain said equation pair $c=c[D_H,D_L]$ and $s=s[D_H,D_L]$; and (c) said second calibration includes substituting said fat tissue f and said lean tissue g for said materials p and q in said general calibration method to obtain said equation pair $f=f[D_H,D_L]$ and $g=g[D_H,D_L]$.

3. The method for performing dual-energy x-ray imaging of a human breast of claim 1 wherein said method includes the additional steps of:

(a) identifying all microcalcification points $c_1(x_k,y_k)$ and all non-microcalcification points $c_1(x_i,y_i)$ in said image $c_1(x,y)$;

(b) constructing a background image B(x,y) where points $B(x_i,y_i)=c_1(x_i,y_i)$ and where points $B(x_k,y_k)$ are interpolated from points $c_1(x_j,y_j)$ around points $c_1(x_k,y_k)$; and (c) subtracting said background image B(x,y) from said image $c_1(x,y)$ to obtain a second order approximation microcalcification image $c_2(x,y)$.

4. The method for performing dual-energy x-ray imaging of a human breast of claim 3 wherein said method includes constructing a new microcalcification image $c_{fg}(x,y)$ by the steps of:

(a) identifying points $(x_m,y_m)$ where an abrupt intensity change in relation to those of adjacent points simultaneously takes place in both said image $f_1(x_m,y_m)$ and said image $g_1(x_m,y_m)$;

(b) calculating a pair of interpolated signal intensities $f_{1a}(x_m,y_m)$ interpolated from points $f_1(x_n,y_n)$ around points $f_1(x_m,y_m)$, and $gia(x_m,y_m)$ interpolated from points $g_1(x_n,y_n)$ around points $g_1(x_m,y_m)$;

(c) verifying that $\Delta f=-[f_1(x_m,y_m)-f_{1a}(x_m,y_m)]$ and $\Delta g=g_{1a}(x_m,y_m)-g_1(x_m,y_m)$ are within a predetermined range of absolute values; and (d) if said $\Delta f$ and said $\Delta g$ are within said predetermined range, setting $c_{fg}(x_m,y_m)$ to either $\Delta f\times R_{cf}$ or $\Delta g\times R_{cg}$;

(e) if either said $\Delta f$ or said $\Delta g$ are not within said predetermined range, setting $c_{fg}(x,y)=0$;

(f) whereby said new microcalcification image $c_{fg}(x,y)$ is constructed based on information in the said first order approximation fat and lean tissue images.

5. The method for performing dual-energy x-ray imaging of a human breast of claim 4 wherein said method includes the additional steps of:

(a) identifying those points $c_{fg}(x_o,y_o)$ whose intensity is zero and those points $c_{fg}(x_m,y_m)$ whose intensity is not zero;

(b) constructing a second order approximation fat tissue image $f_2(x,y)$ where points $f_2(x_o,y_o)=f_1(x_o,y_o)$ and where points $f_2(x_m,y_m)$ are interpolated from points $f_1(x_n,y_n)$ around points $f_1(x_m,y_m)$; and (c) constructing a second order approximation lean tissue image $g_2(x,y)$ where points $g_2(x_o,y_o)=g_1(x_o,y_o)$ and where points $g_2(x_m,y_m)$ are interpolated from points $g_1(x_n,y_n)$ around points $g_1(x_m,y_m)$;

(d) whereby said second order approximation fat tissue image $f_2(x,y)$ and said second order approximation lean tissue image $g_2(x,y)$ are corrected for microcalcification effects.

6. The method for performing dual-energy x-ray imaging of a human breast of claim 4 wherein said x-ray average energy levels are in the range of 16 keV and 100 keV and said predetermined range for said $\Delta f$ and $\Delta g$ is between approximately 10 and approximately 50.

7. The method for performing dual-energy x-ray imaging of a human breast of claim 1 wherein calculating said pair of high-resolution scatter x-ray images $D_{fSHh}(x,y)$ and $D_{fSLh}(x,y)$ includes the steps of:

(a) calculating front low-resolution x-ray images $D_{fHl}(x(i),y(i))$ and $D_{fLl}(x(i),y(i))$ from said images $D_{fHh}(x,y)$ and $D_{fLh}(x,y)$;

(b) determining rear low-resolution primary x-ray images $D_{rPHl}(i,j)$ and $D_{rPLl}(i,j)$ at said rear detector from images of said passed x-rays;

(c) calculating front low-resolution primary x-ray images $D_{fPHl}(x(i),y(i))$ and $D_{fPLl}(x(i),y(i))$ from said images $D_{rPHl}(i,j)$ and $D_{rPLl}(i,j)$;

(d) calculating a front low-resolution scatter x-ray image $D_{fSHl}(x(i),y(i))$ by subtracting said image $D_{fPHl}(x(i),y(i))$ from said image $D_{fHl}(x(i),y(i))$;

(e) calculating a front low-resolution scatter x-ray image $D_{fSLl}(x(i),y(i))$ by subtracting said image $D_{fPLl}(x(i),y(i))$ from said image $D_{fLl}(x(i),y(i))$;

(f) calculating said front high-resolution scatter x-ray image $D_{fSHh}(x,y)$ by interpolating said image $D_{fSHl}(x(i),y(i))$; and (g) calculating said front high-resolution scatter x-ray image $D_{fSLh}(x,y)$ by interpolating said image $D_{fSLl}(x(i),y(i))$.

* * * * *